United States Patent [19]

Browning

[11] 4,114,420
[45] Sep. 19, 1978

[54] ENVIRONMENTAL TEST CHAMBER SYSTEM

[75] Inventor: Charles E. Browning, Dayton, Ohio

[73] Assignee: The United States of America as represented by the Secretary of the Air Force, Washington, D.C.

[21] Appl. No.: 832,708

[22] Filed: Sep. 12, 1977

[51] Int. Cl.² .................................................. G01N 3/18
[52] U.S. Cl. ............................................. 73/15.6; 73/95
[58] Field of Search ................................. 73/15.6, 95

[56] References Cited

U.S. PATENT DOCUMENTS

| 2,350,343 | 6/1944 | Fischer | 73/209 |
| 2,729,967 | 1/1956 | Kaufman | 73/15.6 |
| 3,100,253 | 8/1963 | Connor | 73/15.6 X |
| 3,521,477 | 7/1970 | Dollet | 73/15.6 |
| 3,558,281 | 1/1971 | Dyer | 73/15.6 X |

OTHER PUBLICATIONS

"Vacuum and Controlled Atmosphere Chamber," in R. I. Research, Inc. Bulletin.

Primary Examiner—Herbert Goldstein
Attorney, Agent, or Firm—Joseph E. Rusz; Cedric H. Kuhn

[57] ABSTRACT

A test apparatus comprising an elongated, heat-resistant glass tube, the ends of which are firmly seated in top and bottom end-caps. A plurality of threaded rods extending through the top and bottom end-caps parallel to the glass tube and having nuts threaded on their ends provides means for holding the end-caps in place. The top end-cap has two threaded ports to which fluid inlet and outlet lines are attached while its interior surfaces has an attachment means for supporting a test specimen within the glass tube. The test apparatus is particularly suitable for performing tests on polymeric film or composites under different environmental conditions.

2 Claims, 7 Drawing Figures

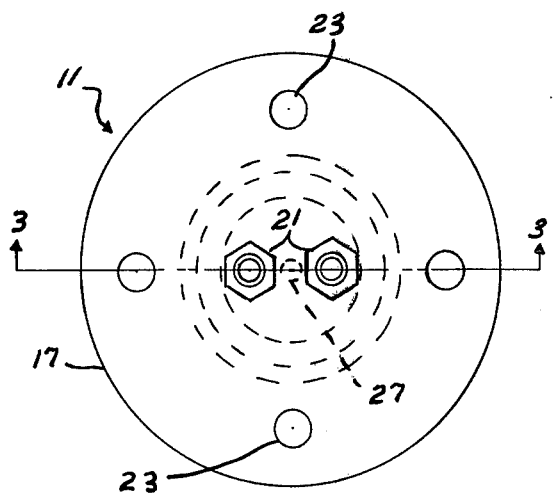
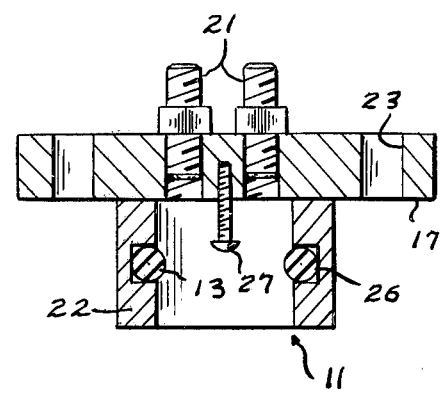
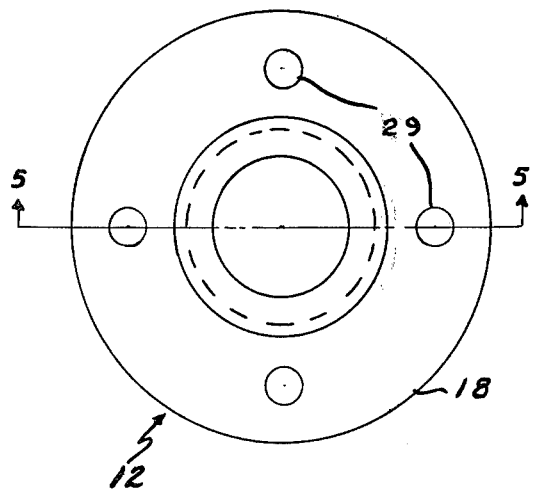
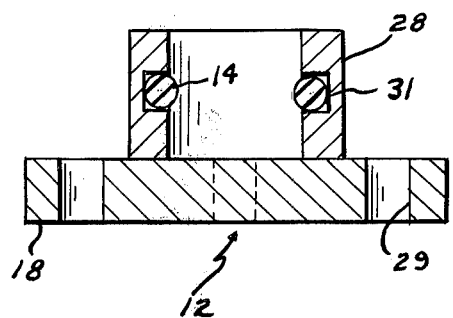

ent invention describes an apparatus for testing polymeric films and composites under different environmental conditions.

ENVIRONMENTAL TEST CHAMBER SYSTEM

RIGHTS OF THE GOVERNMENT

The invention described herein may be manufactured and used by or for the Government of the United States for all governmental purposes without the payment of any royalty.

FIELD OF THE INVENTION

This invention relates to an apparatus for testing polymeric films and composites under different environmental conditions.

BACKGROUND OF THE INVENTION

In the aircraft, automobile and other industries, there is an ever increasing use of plastics and fiber-reinforced composites in the fabrication of components normally made from metals or metal alloys. The conditions encountered in the environment may have a profound influence on the physical properties of polymeric materials. For example, it is known that varying degrees of humidity cause certain properties or polymers, such as creep and stress relaxation, to change to a greater or lesser extent over a period of time. It becomes important, therefore, to provide a means whereby physical properties of polymer test specimens can be determined under different environmental conditions.

It is recognized that the literature is replete with descriptions of apparatus that can be used in performing various tests on test specimens. For example, in U.S. Pat. No. 4,018,080 a device is disclosed whereby it is possible to observe the effects of stress in specimens when tensioned at cryogenic temperatures within an hermetically sealed chamber. In U.S. Pat. No. 3,350,917 the patentees disclose an environmental stress rupture apparatus which includes a means for maintaining a constant stress on a test specimen. Tubes through which a heat transfer medium is circulated are disposed adjacent to each side of the specimen. An absorbent material containing the stress environment is positioned in contact with the heating tubes and with both sides of the specimen. The only environment mentioned in the patent is a surface active agent. While the prior art test apparatus may be suitable for their intended purposes, they are generally complicated in design and often require skilled operators. Moreover, on the basis of present knowledge, none of the known apparatus is capable of measuring physical properties in different environments.

It is a principal object of this invention, therefore, to provide a test apparatus for measuring physical properties of test specimens under different environmental conditions.

Another object of the invention is to provide a device for measuring the elongation of polymeric materials or polymeric based fiber-reinforced composite materials in a moisture environment at temperatures exceeding the boiling point of water.

Other objects and advantages of the present invention will become apparent to those skilled in the art upon consideration of the accompanying disclosure and the drawing, in which:

FIG. 2 is a plan view of the top end-cap of the apparatus of this invention;

FIG. 3 is a cross sectional view taken along line 3—3 of FIG. 2;

FIG. 4 is a plan view of the bottom end-cap of the apparatus of this invention;

FIG. 5 is a cross sectional view taken along line 5—5 of FIG. 4;

SUMMARY OF THE INVENTION

Figure 1:
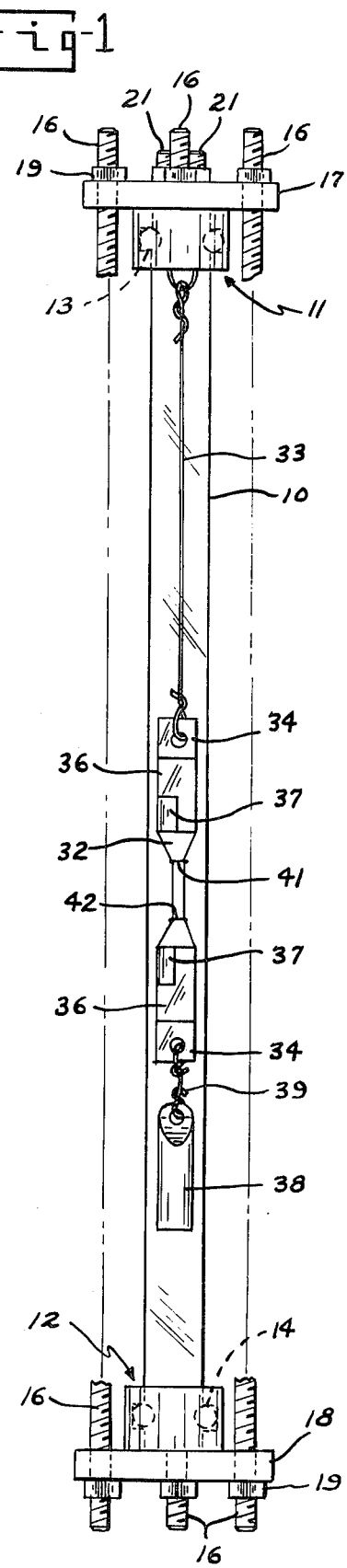
FIG. 1 is an elevational view of the test apparatus of this invention.

The present invention resides in a test apparatus which makes it possible to determine the potential ability of a polymeric material or derived composite material to perform under load in various environments at high temperatures over given periods of time. Broadly speaking, the test apparatus comprises an elongated, heat-resistant glass tube; top and bottom closure members in which the ends of the tube are firmly seated; means for holding the closure members in place; means associated with the top closure member for suspending a test specimen within the glass tube; and fluid inlet and outlet means associated with the top closure member.

The test apparatus of this invention is particularly suitable for performing creep tests on polymeric films or derived composites in a moisture environment exceeding the boiling point of water. Performance of the test with the apparatus, which in effect functions as a pressure vessel, ensures that a constant moisture condition or absorption level and profile is maintained. As a consequence steady-state conditions are achieved, thereby making it possible to obtain test measurements that are not diffusion controlled. It is important to note that use of the glass tube permits creep or strain measurements to be made optically with a device such as a cathetometer. In addition to being especially useful in conducting tests in a moisture environment, the test apparatus can also be used for carrying out tests in other environments such as oxygen, solvents, lubricants, and the like.

For a more complete understanding of the invention, reference is now made to the drawing in which identical reference numerals are used in the figures to designate identical elements.

As illustrated in FIG. 1, the test apparatus includes a thick-walled, heat-resistant glass tube 10. A Pyrex glass tube can be conveniently employed. The upper end of tube 10 is seated in top end-cap 11 while the lower end of the tube is similarly seated in bottom end-cap 12. The two end-caps, preferably formed of stainless steel, function as closure members for the ends of the glass tube. To ensure that the ends of the tube are firmly and tightly positioned in the end-caps, O-rings 13 and 14 disposed in grooves in the interior of each end-cap bear against the outer surface of the glass tube. Tie rods 16 having threaded ends, which extend between and through flanges 17 and 18 of the end-caps, are provided with nuts 19. The function of the tie rods with their nuts tightened against the flanges is to prevent internal pressure in the chamber within the glass tube from forcing off the end-caps. The top end-cap has fittings 21 threaded into openings through its flange 17 to which are attached inlet and outlet lines (not shown) for evacuating the chamber, passing fluids therethrough, and introducing liquids thereinto.

For a better understanding of the structure of the end-caps, reference is now made to FIGS. 2 to 5 of the drawing. As shown in FIGS. 2 and 3, top end-cap 11 is composed of a flange 17 and a hollow cylindrical extension 22. Flange 17 has four openings 23 through which tie rods 16 extend. A groove 26 formed in the inner wall of extension 22 provides a seat for O-ring 13. It is noted that the O-ring and groove are so sized that the O-ring extends a short distance into the interior of the cylindrical extension. Now when glass tube 10 is seated in position in extension 22 with its upper edge in contact with the lower surface of flange 17, the O-ring is depressed or flattened against the surface of the tube. As a result, there is a tight seal between the end-cap and the upper end of the tube.

A bolt or screw 27 is threaded into the lower surface of flange 17 at a point or location where the longitudinal axis of the glass tube intersects the flange. To define the location in another manner, the bolt is positioned in a hole threaded into the under surface of flange that is located in the center of the inner circle formed by the intersection of flange 17 with extension 22. The bolt serves as a means for holding or supporting the chamber formed by the glass tube during the conduct of tests.

As shown in FIGS. 4 and 5, bottom end-cap 12 is composed of flange 18 and a hollow cylindrical extension 28. Flange 18 has four openings 29 which are in vertical alignment with openings 23 in flange 17 (FIGS. 2 and 3) when the end-caps are in position with the tie rods in place as shown in FIG. 1. A groove 31 formed in the inner wall of extension 28 serves as the seat for O-ring 14. Like the O-ring and groove of the top end-cap, O-ring 14 and groove 31 are sized so that the O-ring extends a short distance into the interior of cylindrical extension 28. Upon insertion of the glass tube into the extension with its lower edge in contact with the upper surface of flange 18, O-ring 14 is depressed or flattened against the tube's surface. Thus, the O-rings and the manner in which they are installed ensure a tight seal which prevents fluid egress from or ingress into the test chamber as a result of leakage around the end-caps.

Referring again to FIG. 1, a test specimen 32 is illustrated as being suspended in the test chamber encompassed by glass tube 10 and end-caps 11 and 12. Suspension of the specimen is accomplished by means of wire 33 connected at its upper end to bolt 27 (FIG. 3) and at its lower end to tab 34. Tab 34, attached to the upper end of the specimen, has a hole in its upper portion for attachment of wire 33. Tab 34 is conveniently formed of a strip of thin metal, such as aluminum foil, folded lengthwise upon itself and having a width about equal to that of the "dog bone" specimen. The inner surfaces of the folded aluminum foil are bonded to the outer surfaces of the specimen by means of an anaerobic adhesive. An additional layer or strip 36 of aluminum foil is bonded to each side of the tab in order to lend thickness to the assembly. A spring steel clip 37 is fastened onto layer 36 to ensure that there is no slippage of the specimen.

The lower end of specimen 32 is provided with a tab assembly composed of the same elements described in the preceding paragraph. A weight 38 is suspended from the lower tab by means of wire 39 which is passed through holes in the ends of the tab and weight and then tied.

A more comprehensive understanding of the invention can be obtained by referring to the following example.

EXAMPLE

Two series of creep tests were performed on "dog bone" epoxy resin specimens about 6 mils thick, utilizing the apparatus illustrated in the drawing. This specimen shape was chosen to ensure failures in the gage (narrow) section. As shown in FIG. 1, the gage length was marked with fiducial marks 41 and 42 in the form of boron filament bonded to the specimen with anaerobic adhesive.

The purpose of the tests was to study the elevated temperature behavior of the epoxy as a function of moisture. A test temperature of 300° F. was chosen since this temperature is close to the use temperature while still being lower than the cure temperature.

The test apparatus was mounted in a furnace. After adding double distilled water, the chamber defined by the glass tube and end-caps was evacuated and purged three times with nitrogen by means of inlet and outlet lines connected to the fittings of the top end-cap. Each test was carried out at 300° F., using a cathetometer to monitor movement of the fiducial marks as a function of time. The ultimate stress, $\sigma_u$, used in guiding the tests (1400 psi) was taken from the values found in constant strain rate tensile tests performed at 300° F. after equilibrium exposure at 160° F. at 100% relative humidity.

Because of a slight temperature gradient in the furnace, the upper part of the test chamber was at a slightly higher temperature than the 300° F. temperature maintained just below the surface of the water. There was, therefore, a lower moisture concentration at substantial distances above the water's surface than at and below the surface. This condition was used as a means for testing specimens at two different moisture absorption contents. The amount of moisture absorbed is directly proportional to the relative humidity or moisture concentration. Therefore, performing a creep test under water and substantially above water corresponds to testing specimens of two different moisture contents. The under water test was a "worst" condition that achieved maximum moisture content and is defined as saturation. The above water test achieved lower moisture content and is defined as less than saturation.

Figure 6:
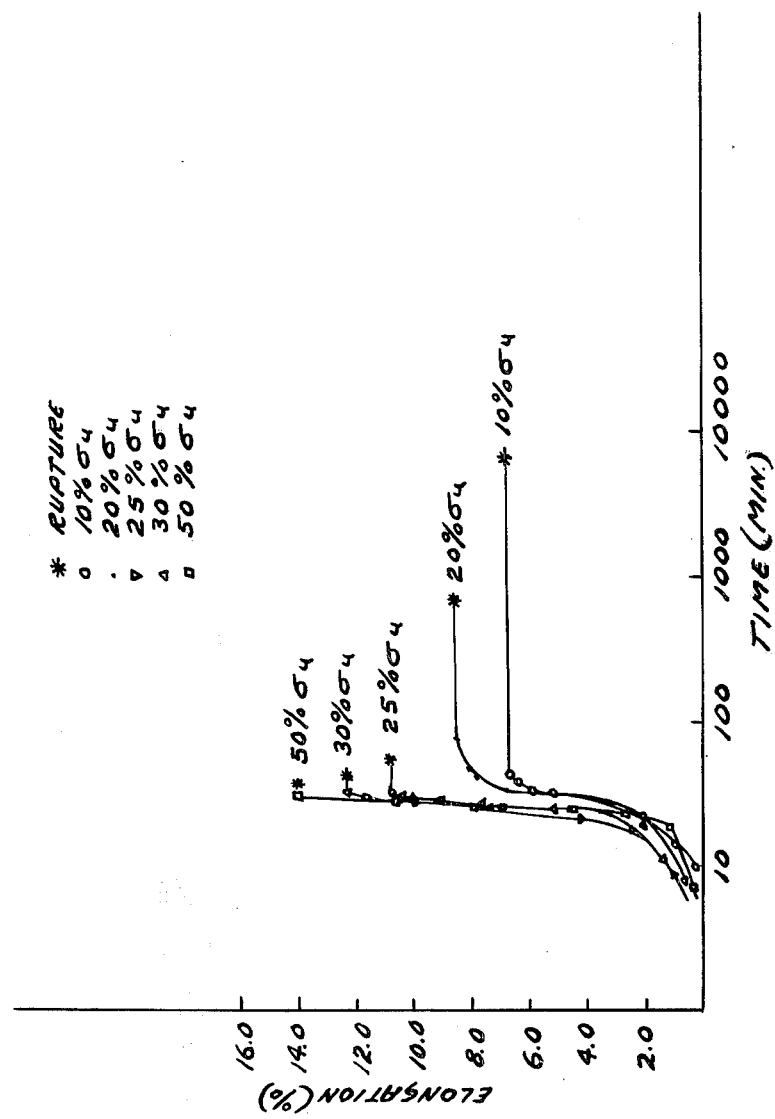
FIG. 6 shows graphically the results of creep tests conducted with the test specimen under water.

The results of the creep tests performed under water at 300° F. are shown graphically in FIG. 6 where percent elongation is plotted versus log time for stresses 10, 20, 25, 30 and 50 percent of ultimate. With increasing stress there was a proportionate increase in elongation and decreased time-to-break.

Figure 7:
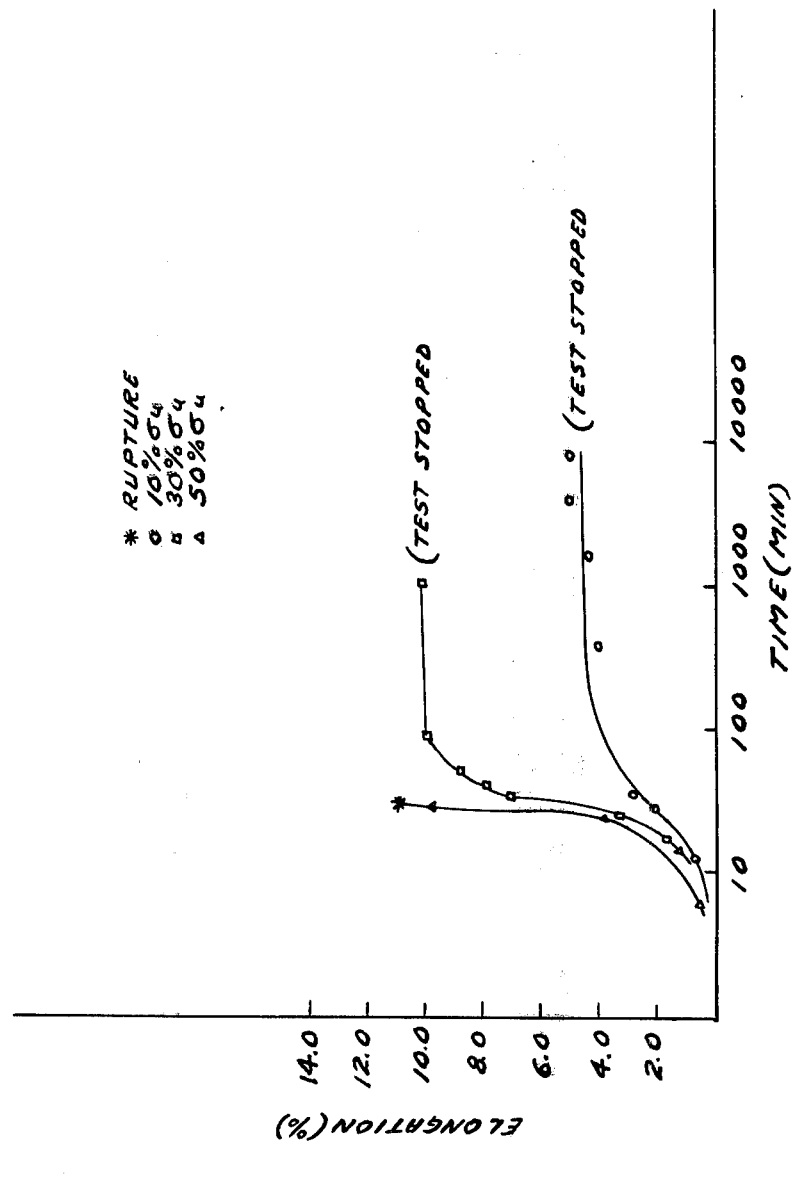
FIG. 7 shows graphically the results of creep tests conducted with the test specimen above water.

The results of creep tests performed at a height of 8 inches above the water level are shown graphically in FIG. 7 where percent elongation is plotted as a function of time. Compared with the under water (saturation) results, the lower moisture concentration (<saturation) yielded lower strains and increased exposure times at equivalent stress levels.

As seen from the foregoing, the test apparatus of this invention makes it possible to measure the elongation of polymeric materials in a moisture environment at temperatures exceeding the boiling point of water. Thus, the potential ability of such materials to perform in a high humidity environment at high temperatures, under load, and over given periods of time can be forecast. However, the test apparatus is not limited to moisture environments; it can be employed in a similar manner for other environments.

As will be evident to those skilled in the art, modifications of the present invention can be made in view of the foregoing disclosure without departing from the spirit and scope of the invention.

I claim:

1. A test apparatus for determining the ability of a polymeric material to perform under load in various environments at high temperatures over given periods of time which comprises a top end-cap composed of a flange attached to a downwardly extending cylindrical member, the flange having holes formed therein around it periphery and the cylindrical member having a first groove formed in and extending around its inner wall; a first O-ring positioned in the first groove; a fastener attached to the lower surface of the flange at a location in the center of the circle formed by the intersection of the flange with the cylindrical member; a bottom end-cap composed of a flange attached to an upwardly extending cylindrical member, the flange having holes formed therein around its periphery and the cylindrical member having a second groove formed therein and extending around its inner wall; a second O-ring positioned in the second groove; an elongated, heat-resistant glass tube vertically disposed and having one of its ends positioned in the cylindrical member of the top end-cap so that its upper edge is in contact with the lower surface of the flange of the top end-cap and its surface is in contact with the first O-ring and having the other of its ends positioned in the cylindrical member of the bottom end-cap so that its lower edge is in contact with the upper surface of the flange of the bottom end-cap and its surface is in contact with the second O-ring; a first wire having one of its ends attached to the fastener and vertically disposed in the tube; one end of a test specimen attached to the other end of the first wire and suspended above the level of water present in the tube; a second wire having one of its ends attached to the other end of the test specimen; a weight attached to the other end of the second wire; inlet and outlet ports formed in the flange of the top end-cap and leading into the chamber formed by the tube and the top and bottom end-caps; tie rods having threaded ends extending through corresponding, vertically aligned holes of the flanges; and nuts threaded onto the ends of the tie rods and tightened against the flange surfaces.

2. The test apparatus according to claim 1 in which the test specimen is immersed in water present in the tube.

* * * * *